United States Patent [19]

Dionne et al.

[11] Patent Number: 5,773,286
[45] Date of Patent: Jun. 30, 1998

[54] INNER SUPPORTED BIOCOMPATIBLE CELL CAPSULES

[75] Inventors: Keith E. Dionne, Rehoboth, Mass.;
Orion D. Hegre, Chepachet, R.I.;
Thomas R. Flanagan, Barrington, R.I.;
Tyrone F. Hazlett, Coventry, R.I.;
Edward J. Doherty, Mansfield, Mass.

[73] Assignee: CytoTherapeutics, Inc., Providence, R.I.

[21] Appl. No.: 449,568

[22] Filed: May 24, 1995

Related U.S. Application Data

[63] Continuation of Ser. No. 176,119, Dec. 30, 1993, abandoned, which is a continuation-in-part of Ser. No. 997,770, Dec. 24, 1992, Pat. No. 5,418,154, which is a continuation-in-part of Ser. No. 722,852, Jun. 28, 1991, abandoned, which is a continuation-in-part of Ser. No. 638,759, Jan. 8, 1991, Pat. No. 5,283,187, which is a continuation-in-part of Ser. No. 461,999, Jan. 8, 1990, Pat. No. 5,158,881, which is a continuation-in-part of Ser. No. 121,626, Nov. 17, 1987, Pat. No. 4,892,538.

[51] Int. Cl.$^6$ ............................. C12N 5/00; C12N 11/00; C12N 11/04

[52] U.S. Cl. ..................... 435/297.1; 424/93.7; 435/174; 435/182; 435/382; 435/395; 435/289.1; 604/890.1

[58] Field of Search ................................ 435/174, 177, 435/180, 182, 188, 240.22, 240.23, 240.242, 297.1, 395, 382, 289.1; 604/890.1; 424/93.7

[56] References Cited

U.S. PATENT DOCUMENTS

| | | | |
|---|---|---|---|
| 4,479,796 | 10/1984 | Kallok | 604/93 |
| 4,892,538 | 1/1990 | Aebischer et al. | 604/891.1 |
| 4,941,874 | 7/1990 | Sandow | 604/60 |
| 5,418,154 | 5/1995 | Aebischer et al. | 435/182 |

FOREIGN PATENT DOCUMENTS

| | | |
|---|---|---|
| WO87/03802 | 12/1986 | WIPO . |
| WO88/10103 | 6/1987 | WIPO . |
| WO90/15637 | 6/1990 | WIPO . |
| WO91/00119 | 7/1990 | WIPO . |
| WO93/00128 | 6/1992 | WIPO . |
| WO93/03901 | 8/1992 | WIPO . |
| WO93/21902 | 4/1993 | WIPO . |

OTHER PUBLICATIONS

Hayashi, Shun–ichi,m and Shirai, Yoshiki, "Development of Polymeric Shape Memory Material," Mitsubishi Technologies Bulletin No. 184, pp. 1–6 (Dec. 1988).

*Primary Examiner*—David M. Naff
*Attorney, Agent, or Firm*—Fish & Neave; Ivor R. Elrifi

[57] ABSTRACT

A biocompatible capsule for containing cells for implantation is prepared containing an inner support that provides tensile strength to the capsule. Cells within the capsule are suspended in a liquid medium or immobilized in a hydrogel or extracellular matrix material, and are surrounded by a semipermeable membrane across which biologically active molecules can be delivered from the capsule to surroundings or from the surroundings into the capsule. The inner support may be formed as an integral part of the capsule during a coextrusion process to form the capsule. Alternatively, the inner support may be a discrete component within a tube having top and bottom sealing fittings that are linked withing the tube by the support. The inner support may have external features such as flutes or a roughened or irregularly-shaped surface, and may be coated with cell-adhesive substance or a cell-viability-enhancing substance. The inner support may be a hollow tube having two channels, one communicating with a filling port that permits injecting cells through the support into the capsule and the other communicating with another port that allows gas to escape through the support as cells are introduced. The capsule may be made immunoisolatory by controlling membrane permselectivity or by substances in the membrane that reduce immune response, and may contain a tether for retrieval that can be formed integrally with the inner support.

10 Claims, 9 Drawing Sheets

INNER SUPPORTED BIOCOMPATIBLE CELL CAPSULES

CROSS REFERENCE TO RELATED APPLICATIONS

The application is a continuation of application Ser. No. 08/176,119, filed Dec. 30, 1993, now abandoned, which is a continuation-in-part of application Ser. No. 07/997,770, filed Dec. 24, 1992, now U.S. Pat. No. 5,418,154, which is a continuation-in-part of application Ser. No. 07/722,852, filed Jun. 28, 1991, now abandoned, which is a continuation-in-part of application Ser. No. 07/638,759, filed Jan. 8, 1991, now U.S. Pat. No. 5,283,187, which is a continuation-in-part of application Ser. No. 07/461,999, filed Jan. 8, 1990, now U.S. Pat. No. 5,158,881, which is a continuation-in-part of application Ser. No. 07/121,626, filed Nov. 17, 1987, now U.S. Pat. No. 4,892,538.

BACKGROUND OF THE INVENTION

This invention relates to cell capsules for the treatment of diseases and disorders with encapsulated cells or substances, such as neurotransmitters, neuromodulators, hormones, trophic factors, growth factors, or other biologically active molecules. In particular, the invention relates to inner supported, biocompatible, cell capsules.

Many diseases or disorders, particularly neurological disorders, appear to be based, in whole, or in part, on the absence or limited availability of such biologically active molecules.

For example, paralysis agitans, more commonly known as Parkinson's disease, is characterized by a lack of the neurotransmitter, dopamine, within the striatum of the brain, secondary to the destruction of the dopamine secreting cells of the substantia nigra.

The direct administration of purified or synthetic dopamine, its precursors, analogs and inhibitors have been studied for therapeutic value in the treatment of Parkinson's disease. These studies have revealed various problems with delivery, stability, dosage, and cytotoxicity of the applied compounds. To date, none of these approaches has demonstrated more than marginal therapeutic value. Brain derived growth factor also may have potential value in the treatment of Parkinson's disease since it has been demonstrated to maintain the viability of striatal neurons in vitro.

Striatal implantation of polymer rods which release sustained amounts of a neurotransmitter, dopamine, has been reported to alleviate experimental Parkinsonism in rodents, indicating that the release of dopamine alone in the proper target structure may be able to correct this functional deficiency.

Similarly, diabetes is a disease characterized by the degeneration of the pancreatic endocrine system with a resulting loss in the body's ability to produce insulin. Although diabetes can be controlled, to an extent, by daily injections of insulin, optimal treatment protocols must take into account the individual's disease state, as well as changes in a subject's metabolism from day-to-day. For these reasons, polymeric matrix delivery systems for insulin have not been particularly successful.

Many other diseases are, likewise, characterized by a deficiency in a critical biologically active molecule that cannot easily be supplemented by injections or longer-term, controlled release therapies. Still other diseases, while not characterized by substance deficiencies, can be treated with biologically active moieties normally made and secreted by cells. Thus, trophic and growth factors may be used to prevent neurodegenerative conditions such as Huntington's and Alzheimer's diseases, and adrenal chromaffin cells which secrete catecholamines and enkephalins have been used to treat pain.

The implantation of living cells capable of constitutively producing and secreting neurologically active factors has been attempted. Remedial transplantation of neurotransmitter-secreting tissue has been accomplished using the patient's own tissue so as not to elicit an immune response. For example, dopamine-secreting tissue from the adrenal medulla of patients suffering from Parkinson's disease has been implanted in their striatum with some success. However, this procedure is only used in patients less than 60 years of age, as the adrenal gland of older patients may not contain sufficient dopamine-secreting cells. This restriction limits the usefulness of the procedure as a remedy since the disease most often affects older people.

Other transplantation approaches have demonstrated that even though the brain is considered "immuno-privileged", rejection ultimately occurs with both allografts and xenografts. This problem necessitates the co-administration of immuno-suppressors, the use of which renders their own set of complications and deleterious side-effects.

One encapsulation approach has been macroencapsulation, which typically involves loading cells into hollow fibers and then sealing the extremities. The encapsulation of such cells by a permselective membrane which permits diffusion of the biological factor restrains the cells within a specific location. Encapsulation may also reduce or prevent host rejection in the case of cross species (xenogeneic) or allogeneic transplantation. However, the macrocapsules in the prior art are somewhat flexible, and susceptible to bending and kinking. Moreover, due to unreliable closure, conventional methods of macroencapsulation have provided inconsistent results.

Various types of cell capsules are known. Aebischer (U.S. Pat. No. 5,158,881) discloses a method for encapsulating viable cells by forming a tubular extrudate around a cell suspension and sealing the tubular extrudate at intervals to define separate cell compartments joined by polymeric links. Dionne et al. (PCT92/03327), discloses a biocompatible, immunoisolatory vehicle. Mandel et al. (WO 91/00119) discloses a semipermeable cell closeable membrane tube for implantation in a subject having a large pore hydrophobic outer surface to encourage vascularization. Aebischer (WO 93/00128) discloses a renewable implant having a U-tube shaped membrane with an external center for aid in insertion.

During the insertion process, the capsules may be subject to compression stresses. Typical insertion schemes include delivery of the capsule to the treatment site via a cannula. It is desirable that the capsule be delivered to the site in an intact condition, so that the cells are retained in the capsule. Once in place, such capsules may be subject to additional stresses, which can cause bending and kinking of the relatively fragile capsule walls. Capsules implanted in the peritoneum, for example, may exhibit such behavior. It is desirable to have a capsule of improved compression strength to withstand compression stresses both during insertion and upon implantation at the target site.

In most instances, it is desirable that such capsules be readily retrieved. In some cases, for example, the therapy may have a defined end point (i.e. delivery of growth hormone). The implanted cells may also become oncogenic or tumor forming. A dose adjustment may require a reduction in the number of implanted cells at specific times. It is therefore desirable to have a capsule with improved tensile strength which may be reliably and completely retrievable. Some of the prior art capsules are not easily retrievable, being prone to breakage upon retrieval. During retrieval, tension is one of the primary stresses on the capsule.

Additionally, there are a variety of factors that may influence the strength of polymeric membranes used to construct macrocapsules. The type of polymer and its molecular weight will have an effect. The membrane geometry, including the fiber wall thickness and the capsule dimensions can be important. The longer the fiber, for instance, the more likely it will develop kinks or twists. Thinner fiber walls, which may be desirable for some applications, may not provide adequate fiber strength. Therefore, some additional type of support may be required.

It is desirable that a capsule not only be of sufficient strength, but that it also be biocompatible. When xenogeneic or allogeneic cells are encapsulated, it is also desirable that the capsule be immunoisolatory.

In some instances, encapsulated cells may form a necrotic core in the center of the capsule. Nutrients must diffuse into the capsule and waste products must be able to leave the capsule for cell viability. Such a core may be due to a shortage of certain metabolites reaching the center of the capsule, or may be due to the build up of toxic products within the core. In these instances, since the central area of the capsule does not support viable cells, and since the necrotic tissue is nonfunctional, the necrotic core may not contribute to the overall function of the implanted capsule. As dying cells accumulate and begin to break down, the necrotic tissue may also release factors which are detrimental to the surviving cells, e.g., factors which elicit a macrophage or other immune response. Additionally, the extra space in the center of the capsules may lead to slower reaction times and to potential overshoot (i.e., overproduction of a biologically active molecule). This is because the larger the necrotic core becomes, the larger the amount of the biologically active molecule (e.g., insulin or other feedback controlled substrate) may be required to obtain an equivalent transmembrane gradient to cause transport of the substrate across the membrane. It may therefore be desirable to eliminate this core.

It is further desirable to utilize capsules having increased surface area to volume ratios and reduced diffusion distances for delivery of the biologically active molecule across the semipermeable capsule jacket.

SUMMARY OF THE INVENTION

The present invention addresses the foregoing problems by providing an inner supported, biocompatible cell capsule that is easily retrievable upon implantation into a recipient animal. The capsules of the present invention have at least one semipermeable surface across which biologically active molecules can be delivered. Delivery of such molecules can be from the capsule to the host, or from the host to the capsule. The inner supported capsules of this invention have increased surface area to volume ratios as well as smaller diffusion distances.

In one embodiment of the invention, the cell chamber is a coaxial single lumen tube assembly with a cylindrical inner support. In this embodiment, the inner support may be made as a result of the coextrusion process used to form the cell chamber. Alternatively, the inner support may be added as a discrete component, linking both sealed ends of the chamber. The support may also be formed integrally with either the top or bottom sealing fitting.

In another embodiment, the inner support is provided with additional external surface characteristics. For example, the inner support may have flutes extending radially along the axis of the cell chamber. Alternately, the external surface of the inner support may be roughened or irregularly-shaped.

In another embodiment, the inner support is hollow, and may be aligned concentrically with a filling port. The inner support tube is provided with openings which communicate with the filling port and also with the cell chamber. In this embodiment, cells can be injected through the filling port and allowed to flow from the support tube into the cell chamber. A second port may also be provided to allow for the escape of air from the chamber as cells are introduced.

DEFINITIONS

As used herein "a biocompatible capsule" means that the capsule, upon implantation in a host mammal, does not elicit a detrimental host response sufficient to result in the rejection of the capsule or to render it inoperable. Such inoperability may occur, for example, by formation of a fibrotic structure around the capsule limiting diffusion of nutrients to the cells therein.

As used herein "an immunoisolatory capsule" means that the capsule upon implantation into a mammalian host minimizes the deleterious effects of the host's immune system on the cells within its core, such that the capsule functions for extended periods of time in vivo.

Biological activity refers to the biological effects of a molecule on a specific cell. As used herein "a biologically active molecule" is one which may exert its biological activity within the cell in which it is made (e.g., bcl-2 to prevent apoptosis) or may be expressed on the cell surface and effect the cell's interactions with other cells or biologically active molecules (e.g., a neurotransmitter receptor or cell adhesion molecule). Additionally, a biologically active molecule may be released or secreted from the cell in which it is made and exert its effect on a separate target cell (e.g., a neurotransmitter, hormone, growth factor, or cytokine).

BRIEF DESCRIPTION OF THE DRAWINGS

Like reference characters in the respective figures indicate corresponding parts.

DETAILED DESCRIPTION

This invention is directed to an improved inner supported, biocompatible cell capsule. The capsule has at least one semipermeable surface across which biologically active molecules can be delivered to the surrounding tissue. The capsule may include means for introducing cells therein following implantation.

The inner supported capsule of the instant invention comprises (a) an inner support, (b) a core which contains a cell or cells, either suspended in a liquid medium or immobilized within a hydrogel or extracellular matrix material, and (c) a surrounding or peripheral region of permselective matrix or membrane (jacket) which does not contain isolated cells and which is biocompatible. If desired, the capsule can be constructed to minimize the deleterious effects of the host's immune system on the cells in its core.

The core of the polymer capsule is constructed to provide a suitable local environment for the continued viability and function of the cells isolated therein. The instant capsule can be used to immunoisolate a wide variety of cells and cell lines, if desired.

Many transformed cells or cell lines are most advantageously isolated within a capsule having a liquid core. For example, cells can be isolated within a capsule whose core comprises a nutrient medium, optionally containing a liquid source of additional factors to sustain cell viability and function, such as fetal bovine or equine serum.

Suitably, the core may be composed of a matrix formed by a hydrogel which stabilizes the position of the cells. The term "hydrogel" herein refers to a three dimensional network of cross-linked hydrophilic polymers. The network is in the form of a gel, substantially composed of water, preferably but not limited to gels being greater than 90% water. Cross-linked hydrogels can also be considered solids because they do not flow or deform without appreciable applied shear stress.

Compositions which form hydrogels fall into three classes for the purposes of this application. The first class carries a net negative charge and is typified by alginate. The second class carries a net positive charge and is typified by extracellular matrix components such as collagen and laminin. Examples of commercially available extracellular matrix components include Matrigel™ and Vitrogen™. The third class is neutral and is typified by crosslinked polyethylene oxide. Alternatively other matrices or spacers, which are not necessarily crosslinked, may also be employed within the core. Alternative matrices include precipitated chitosan, synthetic polymers and polymer blends, microcarriers and the like, depending upon the growth characteristics of the cells to be encapsulated.

The jacket of the capsule may be made of a material which is the same as that of the core, or it may be made of a different material. In either case, the material used results in a surrounding or peripheral region which is permselective and biocompatible. The jacket may also be constructed to be immunoisolatory, if desired.

Various polymers and polymer blends can be used to manufacture the capsule jacket. Polymeric membranes forming the capsule may include polyacrylates (including acrylic copolymers), polyvinylidenes, polyvinyl chloride copolymers, polyurethanes, polystyrenes, polyamides, cellulose acetates, cellulose nitrates, polysulfones, polyphosphazenes, polyacrylonitriles, PAN/PVC, as well as derivatives, copolymers, and mixtures thereof.

The capsule jacket may also include a hydrophobic matrix, such as an ethylene vinyl acetate copolymer, or a hydrophilic matrix such as a hydrogel. Jacket 15 may be post-production coated or treated with an impermeable outer coating, such as a polyurethane, ethylene vinyl acetate, silicon, or alginate covering part of the cell chamber.

The solvents used in conjunction with the above-identified polymers in forming the jacket will depend upon the particular polymer chosen for the membrane material. Suitable solvents include a wide variety of organic solvents, such as alcohols and ketones generally, as well as dimethylsulfoxide (DMSO), dimethylacetamide (DMA), and dimethylformamide (DMF), and blends of these solvents, as well. In general, water-miscible organic solvents are preferred.

The polymeric solution, or "dope", can also include various additives, including surfactants to enhance the formation of porous channels, as well as antioxidants to sequester oxides that are formed during the coagulation process. Exemplary surfactants include Triton-X 100 available from Sigma Chemical Corp., and Pluronics P65, P32, and P18. Exemplary anti-oxidants include vitamin C (ascorbic acid) and vitamin E.

In addition, anti-inflammatory agents, angiogenic factors, and cell growth factors can also be incorporated into the polymeric membrane to reduce immune response or to stimulate cell culture, respectively. Exemplary anti-inflammatory agents include corticoids such as cortisone and ACTH, dexamethasone, cortisol, interleukin-1 and its receptors and agonists, and antibodies to TGF, to interleukin-1, and to interferon-gamma. Exemplary angiogenic factors include fibroblast growth factor and nerve growth factor. Alternatively, these materials can be added to the capsules after manufacture or formation by a post-coating or spraying process. For example, the capsules can be immersed in a solution containing an anti-inflammatory agent, an angiogenic factor, or a growth factor.

Post-coating procedures can also be used to provide a protective barrier against immunogens and the like. For example, after formation, the cell chambers can be coated (e.g., by immersion, spraying or applying a flowing fluid during extrusion, if applicable) with a surface protecting material, such as polyethylene oxide or polypropylene oxide to inhibit protein interactions with the exposed cell chambers. Other protective coatings include silicon, and hydrogels such as alginates. Derivatives of these coating materials may also be used, such as polyethylene oxide-polydimethyl siloxane.

The jacket may be formed freely around the core without chemical bonding or, alternatively, the jacket may be directly cross-linked to the core matrix. In either case, formation of the vehicle of the present invention does not require polymers of opposite charge to the core being present in an interfacial layer or in the jacket, but they can be there.

The jacket allows passage of substances up to a predetermined size, but prevents the passage of larger substances. More specifically, the surrounding or peripheral region is produced in such a manner that it has pores or voids of a predetermined range of size; as a result, the vehicle is permselective. The molecular weight cutoff (MWCO) selected for a particular capsule will be determined in part by the application contemplated.

Figure 1A:
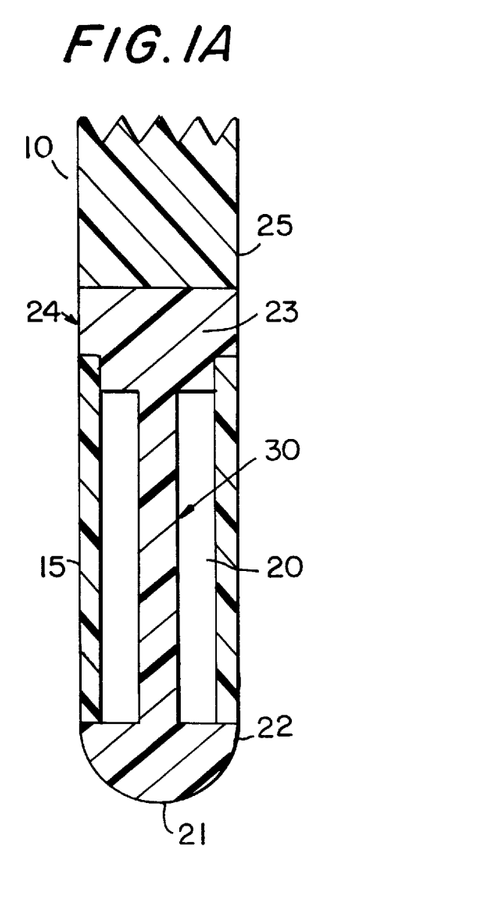
FIG. 1A is a cross-sectional side view of an inner supported capsule of the present invention with the support connected at both ends of the capsule.

Referring to FIG. 1A, one embodiment of capsule 10 comprises a standard single lumen (hollow fiber) cell chamber 20 formed by jacket 15 and sealing fittings 22, 23. Distal tip 21 of cell chamber 20 is sealed with a bottom sealing fitting 22 and proximal tip 23 is sealed with a top sealing fitting 24. A tether 25 is integral with or attached to top sealing fitting 24.

The tether 25 can be post-coated with a material (e.g., a polyurethane or the like) which imparts additional strength to the filament. Such tethered cell capsules can find a variety of applications, particularly which implanted in a subject for delivery of active factors. In use, the cell capsule can be located as close to the target region, or treatment site, (e.g., in the brain, peritoneal cavity or elsewhere) as desired, while the other end of the tether can be fixed at a convenient anchor point or disposal in a readily accessible location for retrieval.

An inner support tube 30 extends between and is connected to fittings 22, 24. Inner support tube 30 reinforces the cell chamber 20 and preferably resides in the center thereof.

The inner support 30 may be made from any material which is substantially non-toxic to cells, and which has a greater tensile strength which is greater than or equal to the tensile strength of jacket 15. Polymeric materials which could be used include acrylates (such as alkaline methacrylates, cyano acrylates, polymethyl acrylate and poly((2-dimethylamino) ethyl methacrylate)), urethanes, silicones, PVC, PAN/PVC, epoxies, etc. Alternatively, inner support 30 may be made of a metal or alloy, such as medical grade titanium or stainless steel. Polymeric or metallic shape memory materials may also be used for the inner support 30 and tether 25. Such polymeric shape memory materials are known. See, e.g., Shirai and Hayashi, *Mitsubishi Technical Bulletin,* 184, pp. 1–6 (1988). Metallic shape memory materials are also known. See, e.g., U.S. Pat. Nos. 4,505,767 and 4,565,589.

Inner support tube 30 may be made as a result of the coextrusion process used to fabricate the cell chamber 20, in cases where the capsule 10 is fabricated in a single step.

Where the capsule 10 is fabricated step-wise, the support 30 may be added as a discrete component, linking seals 22, 24. In such an embodiment, illustrated in FIG. 1C, support 30 is provided with male threads 35, 36 on each end. Both the bottom seal 22 and top seal 24 are provided with female threads 220 and 240 which mate with the threads on support 30. Hollow fiber membrane 15 is sealed at a first end, preferably using an acrylate glue. Support 30 is then inserted into chamber 20 and male thread 35 threaded and sealed into female thread. 220 of bottom seal 22, preferably also with light cured acrylate. Next, cells are added to the chamber 20 and male thread 36 is threaded and sealed into female thread 240, again preferably with acrylate glue.

Figure 1B:
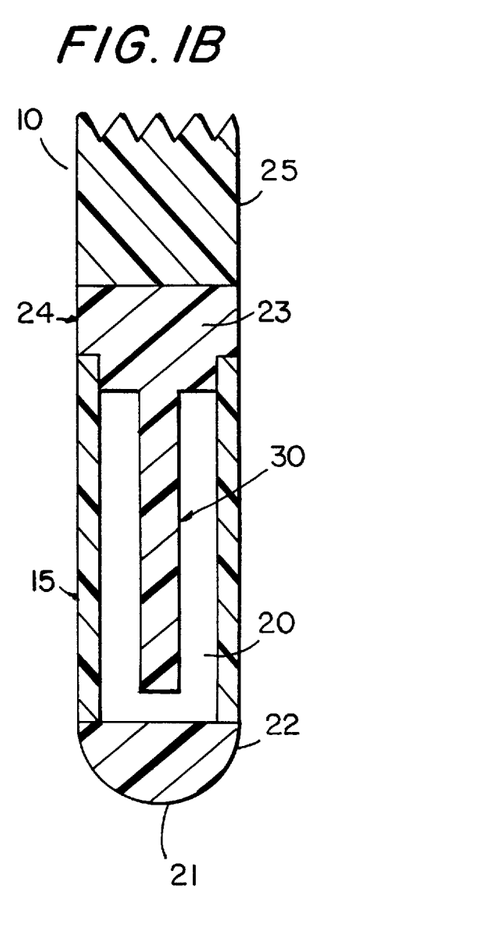
FIG. 1B is a cross-sectional side view of an inner supported capsule of the present invention with the support connected at only one end of the capsule.
Figure 1C:
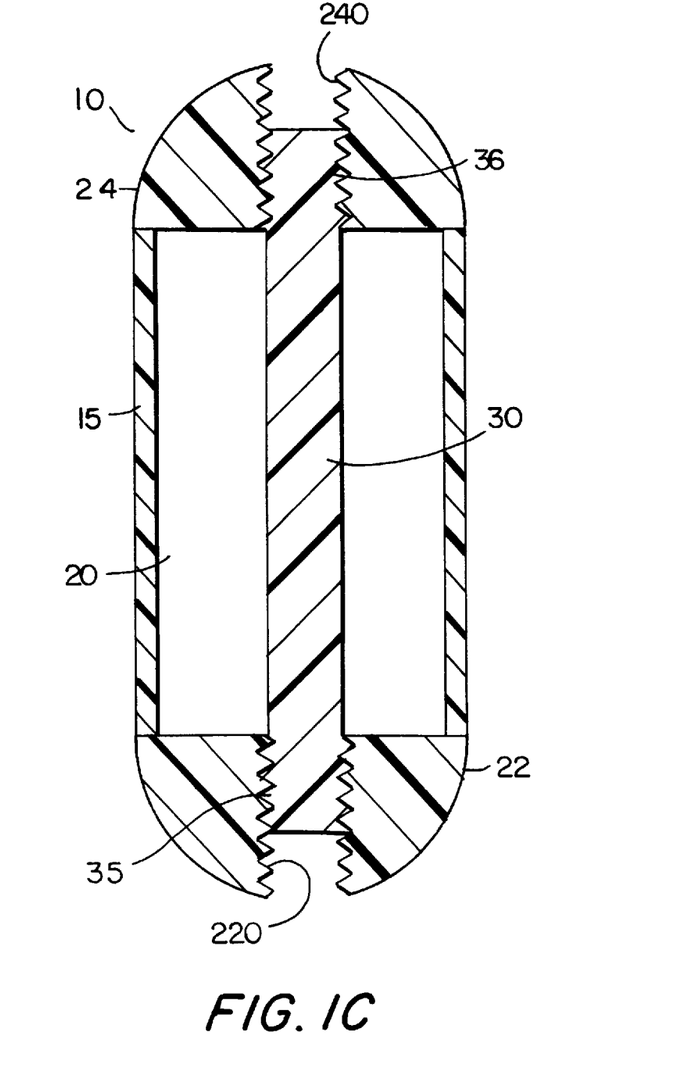
FIG. 1C is a cross-sectional side view of an inner supported capsule of the present invention with a threaded inner support.

As illustrated in the embodiment of FIG. 1B, inner support 30 may be connected to only one of the fittings 22, 24. In this embodiment, the support will serve a space filling function, and may also serve as a reservoir for a substance that enhances cell viability. Inner support 30 will help prevent kinking in capsules constructed according to this embodiment.

Any suitable method of sealing the inner supported capsule may be used, including the employment of polymer adhesives and/or crimping, knotting and heat sealing. These sealing techniques are known in the art. See, e.g., J. Altman et al., "Successful Pancreatic Xenografts Using Semipermeable Membrane", 5 *Artificial Organs (Suppl.)* 776 (1981) (Polyvinylchloride acrylic XM50 copolymer tubing biocompatible epoxy or cyacrylate glue); J. Altman et al., "Long-Term Plasma Glucose Normalization in Experimental Diabetic Rats With Macroencapsulated Implants of Benign Human Insulinomas", 35 *Diabetes* 625, (1986) (poly (acrylonitrile-co-vinyl-chloride) (PAN/PVC) copolymer glue in solvent); B. Dupuy et al., "In Situ Polymerization of membranes around cells": W. Hymer et al., "Pituitary Hollow Fiber Units In Vivo and In Vitro", 32 *Neuroendocrinology* 33 9 (1981) (PAN/PVC fibers syringe loaded, crimping with heated forceps); H. Iwata et al., "The Use of Photocrosslinkable Polyvinyl Alcohol in the Immunoisolation of Pancreatic Islets", 22 *Transplant Proceedings* 797 (April 1990) (Production of encapsulated cells using photocrosslinkable hydrogel); Y. Kojima et al., "Xenogeneic Pancreatic Islet Transplantation Using a Millipore Diffusion Chamber", 19 *Transplant Proceedings* 981 (February 1987) (Millipore MF cement); P. Lamberton et al., "Use of Semipermeable Polyurethane Hollow Fibers for Pituitary Organ Culture", 24 *In vitro Cellular & Developmental Biology* 500 (June 1988); C. Lum et al., "Intraperitoneal Nucleopore Chambers: a Murine Model for Allograft Rejection", 20 *Transplant Proceedings* 173 (April 1988) (Nucleopore membranes attached with silicone sealant; Millipore MF cement); S. Ronel et al., "Macroporous Hydrogel Membranes for a Hybrid Artificial Pancreas", 17 *J. Biomed. Materials Res.* 855 (1983) (Pressure/heat sealing of hydrogel cell capsules); N. Theodorou et al., "Problems int he Use of Polycarbonate Diffusion Chambers for Syngeneic Pancreatic Islet Transplantation in Rats", 18 *Diabetologia* 313 (1980) (Polycarbonate filters sealed with polyacrylic cement); F. Wong et al., "Effects of Thymus Enclosed in Millipore Diffusion Envelopes on Thymectomized Hamsters", 28 *Blood* 40 (1966); and G. Zondervan et al., "Design of a Polyurethane Membrane for the Encapsulation of Islets of Langerhans", 13 *Biomaterials* 136 (1992) (Polyurethane tubing sealed by knotting).

In addition, any suitable "dry" sealing method can also be used. In such methods, a substantially non-porous fitting is provided through which the cell-containing solution is introduced. Subsequent to filling, the capsule is sealed. Such a method is described in U.S. application Ser. No. 08/082,407, filed Jun. 23, 1993, now abandoned, herein incorporated by reference.

Alternately, support 30, which extends perpendicular to the body of fittings 22, 24, may be formed integrally with either one of the fittings. In such an embodiment, the fitting and support to which it is integrated are first secured to jacket 15, as discussed above. Next, cells are added to chamber 20 and the opposite end of the chamber 20 is then sealed with the other fitting, such that the seal is also attached to the support 30.

In cases where fittings 22, 24 and the support 30 are integral, one fitting may also contain a port for introducing cells. In such cases, the capsule 10 may be preassembled, having one end completely sealed, and the fitting containing the port attached to the opposite end. Cells are then introduced in the chamber 20, and the opening is then sealed.

When a capsule is implanted, there is strain between the implant and movable tissue in the host recipient. For example, human brain can move within the cranium. The chamber 20 can be manufactured from a flexible material to allow the capsule to compensate for such movement.

Various methods for forming capsules are known in the art. One such method, disclosed in WO 93/00063, incorporated herein by reference, involves coextrusion of a polymeric casting solution and a coagulant (which can include biological tissue fragments, organelles, or suspensions of cells and/or other therapeutic agents). Following extrusion, the polymeric solution preferably forms a semipermeable membrane upon coagulation. The membrane is a porous structure.

The permeability of the polymeric membrane can be varied by controlling the viscosity of the polymeric casting solution such that upon coagulation, the coating will form with a network of microchannels to provide diffusion pathways. In one embodiment, this can be achieved by employing a water-miscible solvent as a component of the polymeric solution and maintaining a pressure differential between the coagulant and the polymeric solution during extrusion. As the tubular extrudate forms, water from the coagulant infiltrates into the coagulating polymer to replace the solvent as the solvent is driven outward by the pressure difference. Upon coagulation, the water which has infiltrated into the polymeric membrane provides a network of pores. The optimal pressure and viscosity varies with the solvent and polymer employed, but can readily be ascertained for any particular polymer/solvent combination by those skilled in the art without undue experimentation.

Figure 2:
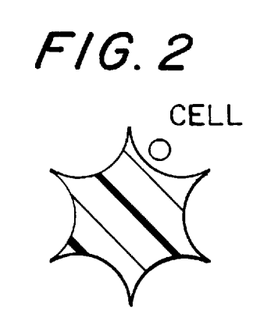
FIG. 2 is top cross-sectional view of a fluted inner support.
Figure 3:
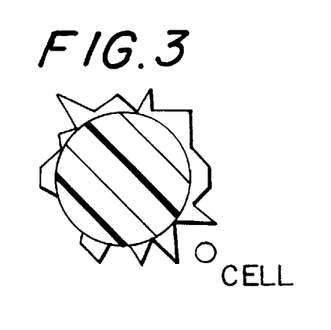
FIG. 3 is a top cross-sectional view of roughened or irregularly-shaped inner support.

In another embodiment, shown in FIG. 2, the external surface of the inner support 30 is fluted. The flutes of the inner support 30 extend radially along the axis of the chamber 20. Such a design increases the surface area of the inner support, which may be beneficial to some cell types. Alternatively, as shown in FIG. 3, the external surface of the inner support 30 may be roughened. This feature may help keep cells distributed throughout the unoccluded lumen space.

Figure 4:
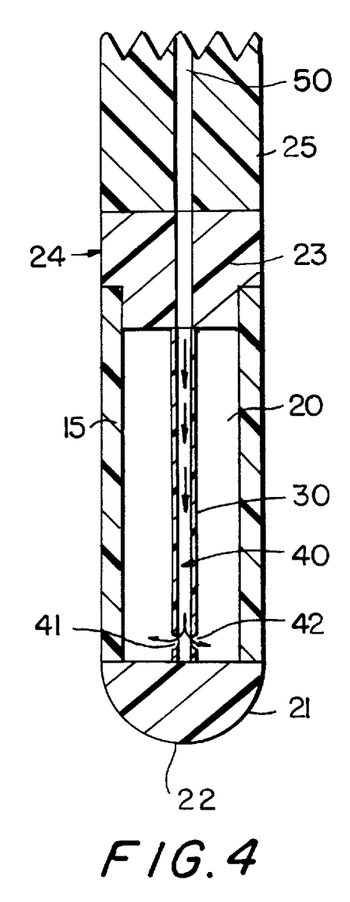
FIG. 4 is a cross-sectional side view of a capsule having a hollow inner support forming a channel, into which a cell suspension can be injected and allowed to flow into the lumen.

In a further embodiment, as illustrated in FIG. 4, the inner support 30 may be hollow, defining a channel 40. The channel 40 may be aligned concentrically with a filling port 50 provided through the tether 25 and the top fitting 24. The support 30 has openings 41, 42 which communicate with channel 40 and the interior of the chamber 20. In such a configuration, cells can be injected through port 50 and allowed to flow from channel 40 into chamber 20. In capsules containing such a hollow support 30, substances such as growth or trophic factors, which help sustain the cells may be inserted into the channel 40, after the cells have been introduced into the chamber 20. A second port may also be provided through tether 25 and top fitting 24 to allow for the escape of air from chamber 20 as cells are introduced through port 50 and channel 40.

Figure 5:
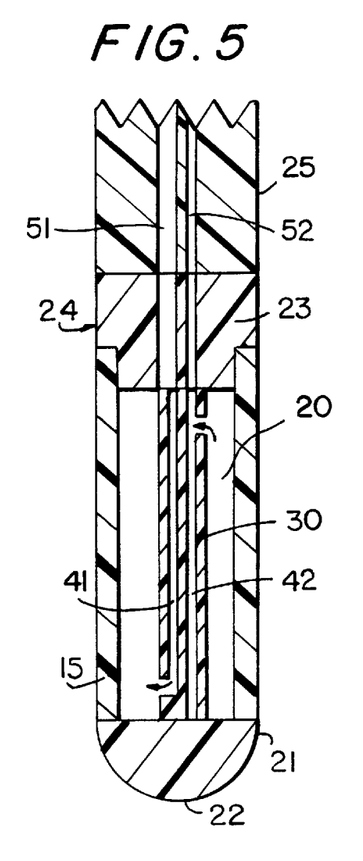
FIG. 5 is a cross-sectional side view of a capsule having a channeled inner support as in FIG. 4, and additionally having a second port to allow for escape of air.
Figure 6:
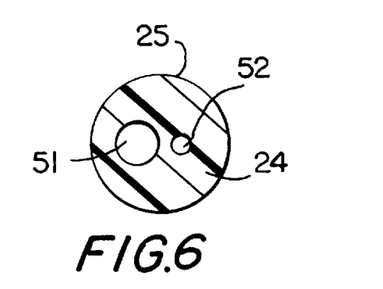
FIG. 6 is a top cross-sectional view of the inner support of FIG. 5.

Another embodiment in which the inner support tube 30 is hollow is illustrated in FIGS. 5 and 6. Inner support tube 30 defines two channels 41, 42. Cells can be injected through port 51 and allowed to flow from channel 41 into the chamber 20. The walls of support 30 may be permeable, and the support 30 may be continuous with a reservoir containing substances which are known to enhance cell viability, such as perfluorocarbons.

Substances which help sustain the cells, as described above, may be inserted into the chamber 20 through port 51 provided through tether 25 and fitting 24 and then through channel 41, after the cells have been introduced into the chamber 20. A second port 52 is also provided through tether 25 and top fitting 24, and aligns with channel 42 of support 30 to allow for the escape of air from chamber 20.

It will be appreciated that the inner supported capsules of the present invention may have a variety of shapes.

The capsule may use hollow fibers for encapsulation or may be in the form of a flat sheet capsule. Using the flat sheet capsule, a first permselective, porous, sheet membrane, having a first interior surface, and a second permselective, porous, sheet membrane, having a second interior surface, are mounted to engaging surfaces of a scrim or wire mesh support positioned between the membranes, such that the membranes are spaced-apart from each other, the interior surfaces of the membranes are oriented to face each other, and the membranes and support define a chamber. The support may be formed with an inner surface defining an access port extending through the fitting. Cells may then be introduced through the access port, and the seal completed with a plug inserted into the port.

When tether 25 is to be used as an aid in fixing and retrieving the capsule 10, it may be desirable to have the inner support 30 integral to tether 25. This eliminates the additional step of attaching tether 25 to the capsule 10. Additionally, since these capsules are generally loaded through a cannula system, it is desirable to use as small a diameter cannula as practicable to minimize tissue damage to the recipient. Forming inner support 30 integral with tether 25 eliminates the need to slip tether 25 over top fitting 24 for attachment, thereby reducing the overall diameter of capsule 10. A seamless juncture between inner support 30 and tether 25 will also improve overall strength of the capsule 10.

The inner supported capsules of the present invention provide improved strength against compression stress, which is the primary type of stress that occurs during insertion of the capsule. The capsule may also undergo some tensile stress and some shear stress, as well as some bending, both during and after implantation.

One primary stress encountered by the capsule 10 during retrieval is tension. As the inner support 30 is formed integrally with at least one fitting 22, 24 of the capsule 10, and is formed of a material which has a tensile strength at least equal to the tensile strength of jacket 15, inner support 30 illustrated in the various embodiments will be used to bear much of the load instead of the jacket 15.

Inner supported capsules will have both increased surface-to-volume ratios as well as smaller diffusion distances.

A wide variety of cells may be used in this invention. These include well known, publicly available immortalized cell lines as well as dividing primary cell cultures. Examples of publicly available cell lines suitable for the practice of this invention include, baby hamster kidney (BHK), chinese hamster ovary (CHO), mouse fibroblast (L-M), NIH Swiss mouse embryo (NIH/3T3), African green monkey cell lines (including COS-a, COS-7, BSC-1, BSC-40, BMT-10 and Vero), rat adrenal pheochromocytoma (PC12) and rat glial tumor (C6). Primary cells that may be used according to the present invention include, bFGF-responsive neural progenitor-stem cells derived from the CNS of mammals (Richards et al., *PNAS* 89, 8591–8595 (1992); Ray et al., *PNAS* 90, 3602–3606 (1993)), primary fibroblasts, Schwan cells, astrocytes, β-TC cells, Hep-G2 cells, AT T20 cells, oligodendrocytes and their precursors, myoblasts, adrenal chromaffin cells, and the like.

The choice of cell depends upon the intended application. The encapsulated cells may be chosen for secretion of a neurotransmitter. Such neurotransmitters include dopamine, gamma aminobutyric acid (GABA), serotonin, acetylcholine, noradrenaline, epinephrine, glutamic acid, and other peptide neurotransmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor.

The encapsulated cells can also be chosen for their secretion of hormones, cytokines, growth factors, trophic factors, angiogenesis factors, antibodies, blood coagulation factors, lymphokines, enzymes, and other therapeutic agents or agonists, precursors, active analogs, or active fragments thereof. These include enkephalins, catecholamines, endorphins, dynorphin, insulin, factor VIII, erythropoietin, Substance P, nerve growth factor (NGF), Glial derived Neurotrophic Factor (GDNF), platelet-derived growth factor (PDGF), epidermal growth factor (EGF), brain-derived neurotrophic factor (BDNF), neurbtrophin-3 (NT-3), an array of fibroblast growth factors, and ciliary neurotrophic factor.

Alternatively, one or more biologically active molecules may be delivered into the capsule. For example, the capsule may contain one or more cells or substances which "scavenge" cholesterol, or other biologically active molecules, from the host.

In some aspects of the invention, the cell is allogeneic (i.e., cells from another of the same species as the subject in which it is to be implanted), autologous or syngeneic (from the same individual), or xenogeneic (i.e., cells from another of a different species).

The recipient may be any suitable animal, preferably a mammal, most preferably a human.

It may also be desirable to encapsulate multiple cell types within a capsule. In one instance, a first type of cell may have an augmentary effect on substance secreting cells of a second type, after the method of Aebischer (U.S. Pat. No 5,182,111). In another instance, it may be desirable to coencapsulate two or more cell types which may both secrete a desired biologically active substance.

The aqueous cell suspensions in cell chamber 20 can further include various additives to protect the cells during the extrusion process or to stimulate their growth subsequently. Such additives may include, for example, a nutrient medium or growth factors which are incorporated into the aqueous suspension, as well as an anchorage substrate material to enhance cell attachment. The anchorage substrate material can be, or can contain, a proteinaceous material, such as collagen, laminin, Matrigel, Vitrogen, or polyamino acids. Alternatively, the cell suspension or the polymeric solution (or both) can include a foaming agent or a blowing agent which can distort the inner surface of the polymeric coating to increase the anchorage surface area of the tubular interior.

In order that this invention may be better understood, the following examples are set forth. These examples are for purposes of illustration only, and are not to be construed as limiting the scope of this invention in any manner.

EXAMPLES

Example 1

Strength Test

The tensile and compression strength of an inner supported capsule was compared with that of a capsule having no inner support.

The capsule without any inner support was constructed using a PAIN fiber—a double-skinned membrane cast from a dope of 12½%(w/w) PAN/PVC in DMSO, having a typical outside diameter of 900 microns and an inside diameter of 750 microns. As shown in Table I, the (tensile) yield point of the capsule is approximately 1.5±0.2 mPa, the (tensile) break point is approximately 2.0±0.2 mPa, the % (tensile) elongation is 55±3, and the (compression) yield point is 1.0±0.4 mPa. However, in a capsule containing a polyurethane inner support (500 μm outside diameter), the (tensile) yield point ranged between approximately 5.3 and 7.5 mPA, the (tensile) break point ranged between approximately 7.1 and 10.5 mPA, the % (tensile) elongation ranged between approximately 50 and 55, and the (compression) yield point was approximately 2.2±0.6 mPa.

TABLE I

Tensile and Compression Data for
Empty Fibers and Inner Supported Fibers

| Fiber Type | Tensile | | | Compression |
| --- | --- | --- | --- | --- |
| | Yield Point (mPa) | Break Point (mPa) | % Elongation | Yield Point (mPA) |
| PAIN fiber only (n = 6) | 1.5 ± 0.2 | 2.0 ± 0.2 | 55 ± 3 | 1.0 ± 0.4 |
| PAIN fiber with support (n = 3) | 5.3, 7.5, 7.5 | 7.1, 9.5, 10.5 | 50/55/52 | 2.2 ± 0.6 |

There is a 350–500% increase in tensile strength with the inner support in place. The fiber elongation was basically held constant—however, the energy required to reach that elongation increased considerably.

If an increase in strength of more than 500% is required, this can be achieved by changing the durometer of the polyurethane or by using different materials for the inner support 30.

There is also an improvement in compression strength of the capsule when an inner support 30 is used. This indicates that there is less of a chance of damaging the jacket 15 during the insertion process.

Example 2

Durability Test

Inner supported capsules, ranging in length from 6 cm to 16 cm were implanted for 18 days in dogs. Two types of inner supports were used: (1) finned silicone rods of 85 shore A durometer, having a central 2 mm rod with four 0.5 mm fins at 90° angles, and (2) silicone tubing (2.5 mm outside diameter) with a stainless steel wire inserted through the center of the tubing.

The inner supports were inserted into the lumen of a 3 mm inside diameter, double skin PAN/PVC fiber which was otherwise too weak to be self-supporting (e.g., the membrane tube would collapse if drained of water and would kink if segments longer than 1 cm were held at one end and held in open air). After insertion, the shell region between the support and the membrane was filled with 1% alginate (Kelco), which was crosslinked by immersion for 6 minutes in 1% $CaCl_2$ solution. The ends of the capsules were sealed by dipping the fiber ends in a solution of 85% DMSO/15% water for 15 seconds, wicking off the excess solvent, injecting polymer glue (12% PAN/PVC in DMSO) and heating the ends by touching them for 2 seconds with a sterile forceps heated to 250° F.

The capsules were implanted in the peritoneal cavity of a normal dog. Normally, after a couple of days, non-inner supported fibers of this length and this strength would be ripped in several places, completely folded over on each other and enmeshed in a ball of fibrous tissue.

After 18 days, the inner supported fibers were removed and found to be completely intact. No rips or major folds were found. The extent of trauma was limited to small kinks and wrinkles along the fiber. No macroscopic damage was observed to any of the peritoneal organs upon removal of the fibers.

Example 3

Retrieval Test

The increase in strength imparted to the capsules by the use of an inner support was also evaluated using a retrieval test. Nine prior art capsules (three each of three types of lumen fiber) and nine inner supported capsules (three each of three types of lumen fiber) were placed in liquid gelatin at ambient temperature. Each capsule was placed approximately 4 cm in the gelatin, with approximately 1 cm remaining outside the gelatin.

The gelatin had been prepared at twice the normal concentration. After the capsules were placed in the liquid gelatin, the gelatin was then refrigerated for approximately four hours. The outer pores of the capsules were penetrated by the liquid gelatin prior to cooling. This was done in order to simulate some form of tissue ingrowth which may happen in vivo.

Each of the non-inner-supported capsules was then removed from the gelatin using forceps. Four of the nine non-inner-supported capsules broke. One of these capsules broke 1 cm from the end placed within the gelatin, two broke 2 cm from the end placed within the gelatin, and one broke 3 cm from the end placed within the gelatin.

Each of the inner-supported capsules was removed from the gelatin by hand using the exposed part of the inner support. None of the inner supported capsules broke upon retrieval. The data is shown in Table II.

TABLE II

| Sample | Supported/ Unsupported | Break/ No-Break | Location of Break |
|---|---|---|---|
| Type 1 HF42293-2 | Unsupported | Break | = 2 cm from end within the Jell-O |
| Type 1 HF42293-2 | Unsupported | Break | = 3 cm from end within the Jell-O |
| Type 1 HF42293-2 | Unsupported | No-Break | |
| Type 1 HF42293-2 | Supported | No-Break | |
| Type 1 HF42293-2 | Supported | No-Break | |
| Type 1 HF42293-2 | Supported | No-Break | |
| Type 2 CP11-93-008 | Unsupported | Break | = 1 cm from end within the Jell-O |
| Type 2 CP11-93-008 | Unsupported | Break | = 2 cm from end within the Jell-O |
| Type 2 CP11-93-008 | Unsupported | No-Break | |
| Type 2 CP11-93-008 | Supported | No-Break | |
| Type 2 CP11-93-008 | Supported | No-Break | |
| Type 2 CP11-93-008 | Supported | No-Break | |

TABLE II-continued

| Sample | Supported/ Unsupported | Break/ No-Break | Location of Break |
|---|---|---|---|
| Type 4 CP11-93-0011 | Unsupported | No-Break | |
| Type 4 CP11-93-0011 | Unsupported | No-Break | |
| Type 4 CP11-93-0011 | Unsupported | No-Break | |
| Type 4 CP11-93-0011 | Supported | No-Break | |
| Type 4 CP11-93-0011 | Supported | No-Break | |
| Type 4 CP11-93-0011 | Supported | No-Break | |

Example 4

Increased Surface Area To Volume Ratio

The following calculations demonstrate that inner supported capsules have a higher surface area to volume ratio than comparative capsules without an inner support.

Figure 7A:
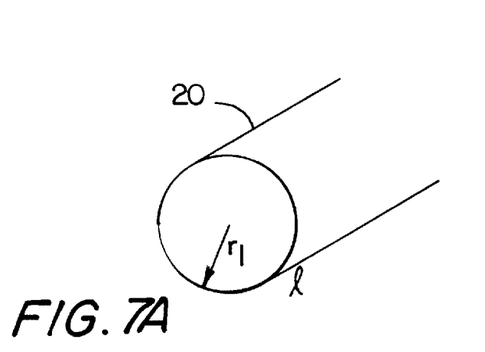
FIG. 7A is a side perspective view of a non-inner supported capsule.

As illustrated in FIG. 7A, given a known volume of tissue $V_t$, a fixed capsule length, l, and an inner radius $r_1$ for a capsule with no inner support, the following equations hold:

$$V_{t1} = \pi r_1^2 l;$$

$$S = 2\pi r_1 l; \text{ and}$$

$$S/V_{t1} = 2/r_1$$

Figure 7B:
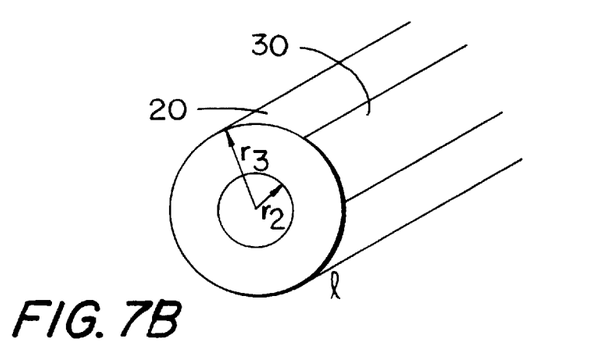
FIG. 7B is a side perspective view of an inner supported cell capsule.
Figure 8A:
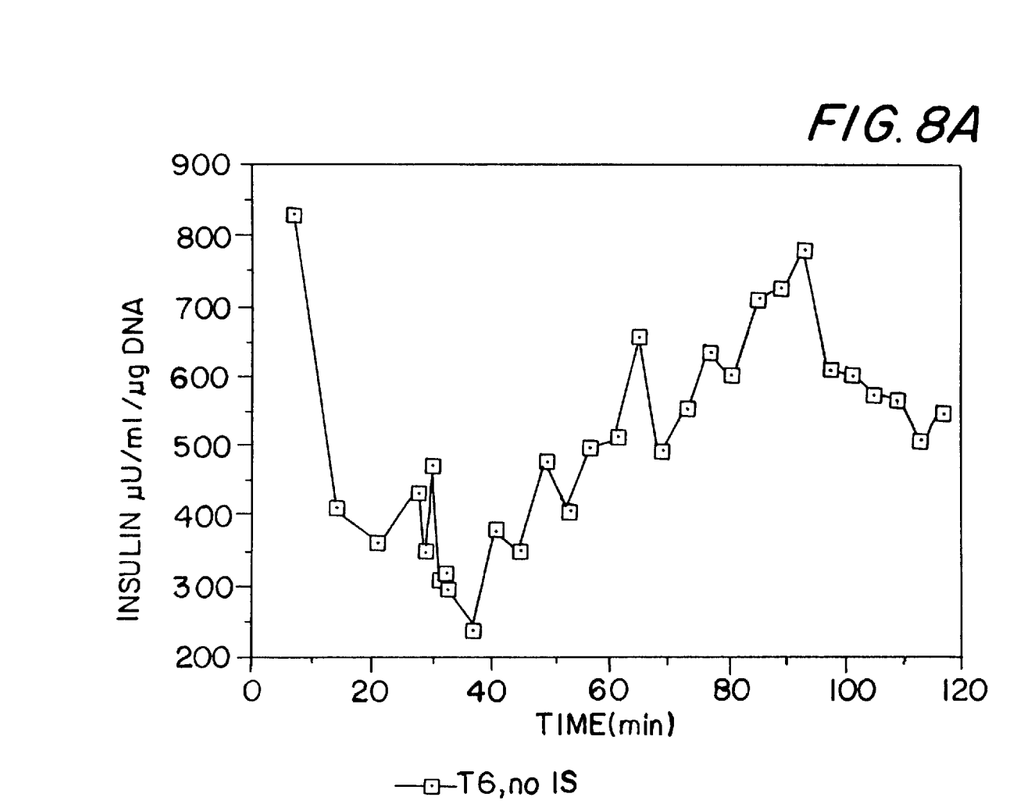
FIGS. 8A–8D are graphs in which insulin production by rat islet cell aggregates (ICAs) is plotted as a function of time. Results are shown for: ICAs in capsules without an inner support (FIG. 8A); ICAs in capsules with an inner support (FIGS. 8B, 8C): and for controls having an alginate core and an inner support but no semipermeable capsule jacket (FIG. 8D).
Figure 8B:
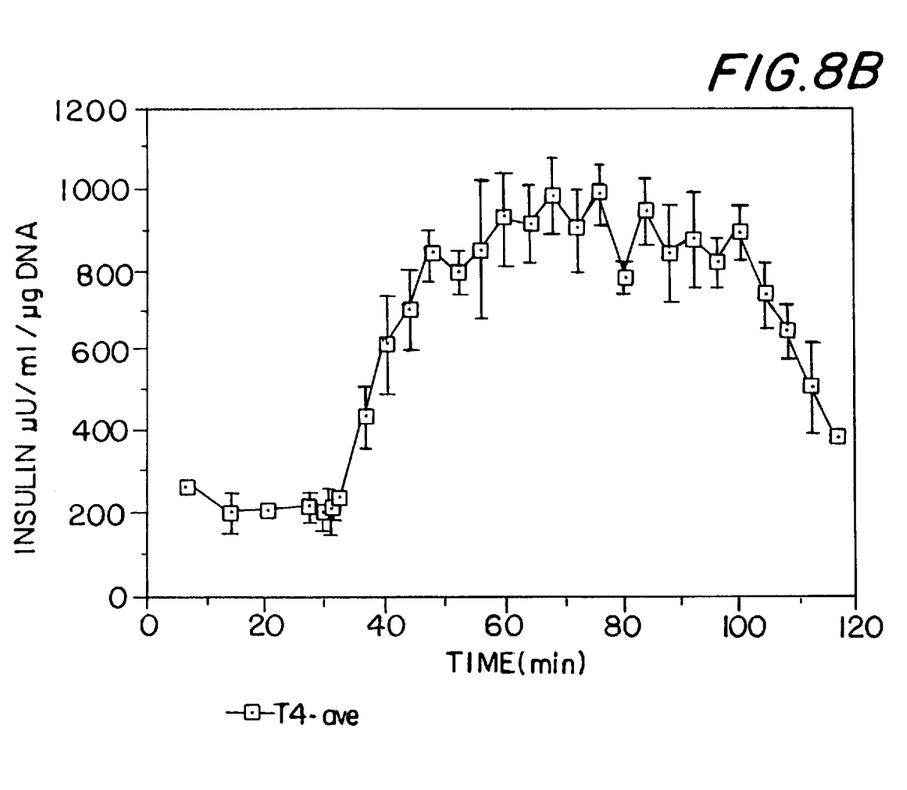
Figure 8C:
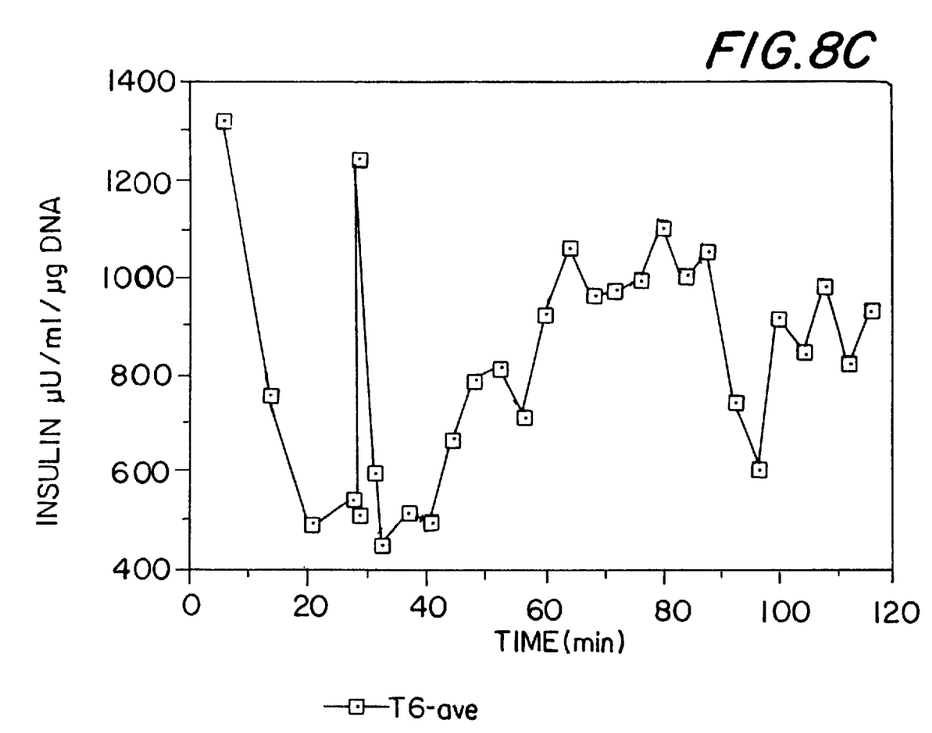
Figure 8D:
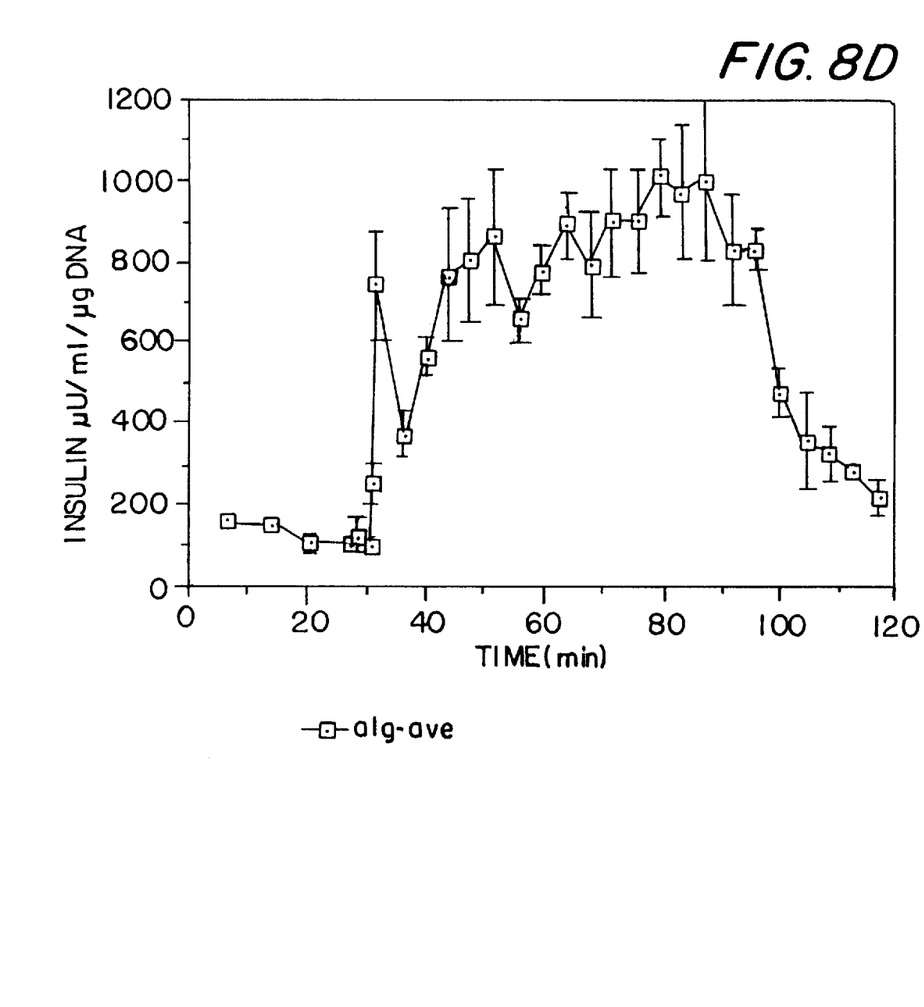

By comparison for the capsule 10 illustrated in FIG. 7B, which has an inner radius $r_3$ for the capsule and with a radius $r_2$ for the outside radius of the inner support 30, the following equations hold:

$$V_{t2} = \pi (r_3 - r_2)^2 l;$$

$$S = 2\pi r_3 l; \text{ and}$$

$$S/V_{t2} = 2r_3/(r_3 - r_2)^2$$

If $r_1 = r_3$, and $r_2$ is greater than zero, the surface area to volume ratio $(S/V_t)$ for the inner supported capsule of FIG. 7B will always be greater than the surface area to volume ratio $(S/V_t)$ for the non-inner supported capsule of FIG. 7A. If, for example, $r_1 = 250$ $\mu$m and $r_2 = 125$ $\mu$m, then $S/V_{t2} = (1.56) S/V_{t1}$.

Where $r_1 = r_2$, and $V_{t1} = V_{t2}$, $r_3 = 1.44 r_2$. This means that if $r_1$ is 250 $\mu$m (providing a 500 $\mu$m inside diameter), the equivalent volume inner supported capsule has $r_3 = 360$ $\mu$m (for an inside diameter of 720 $\mu$m), with an increase in S/V of 1.44.

Example 5

Reduced Diffusion Distance

The following demonstrates that inner supported capsules have a reduced diffusion distance than comparative capsules without an inner support.

Cells loaded in the capsule of FIG. 7A will have a maximum diffusion distance of 250 $\mu$m. In the capsule illustrated in FIG. 7B cells will have a maximum diffusion distance of 110 $\mu$m. Therefore, the maximum diffusion distance for the inner supported capsule of FIG. 7B is less than half the maximum diffusion distance of the capsule of FIG. 7A.

Note that the loading density is higher in the capsule without an inner support. For example, using the capsule dimensions given above (i.e., where $r_1=r_2$), loading the equivalent number of cells in a capsule without an inner support results in a 3-fold increase in tissue loading density compared to the same capsule with an inner support. However, the S/V ratio of the inner supported capsule is increased by a factor of 1.56 and the overall maximum diffusion distance is decreased by a factor of 2.

Example 6

Lewis Rat Test

Three cm long, 2 mm diameter, finned silicon supports (as in example 2) were inserted into the lumen of 3.0 mm inside diameter, double skinned PAN/PVC membranes to form inner supported transplantation chambers. Rat islet aggregates (ICA's) were prepared by collagenase isolation of rat islets, Ficoll™ purification and controlled trypsinization of purified islets. Cell clusters ranging from approximately 1–100 cells were obtained and cultured overnight. These ICAs were suspended in 1% sodium alginate (Kelco) and injected into the shell space between the inner support and the PAN/PVC membrane. After injection, the alginate was crosslinked by immersion of the capsule into 1% $CaCl_2$ for 6 minutes. The ends were sealed with PAN/PVC, as described in example 2 above.

Alternatively, one end of PAN/PVC membrane was sealed, islet/alginate slurry was injected so as to fill ½ of the fiber volume starting at the sealed end, and the polyurethane supports made by sealing both ends of 1.5 mm outside diameter polyurethane tubing inserted into the center of the open end of the fiber so as to displace the alginate/islet slurry pushing it into the space between the inner support and the surrounding membrane. The alginate was then crosslinked and the remaining open end of the capsule was then sealed.

The capsules were implanted IP into male Lewis rats which had been made diabetic by the injection of Streptozotocin such that their non-fasting blood glucose levels were greater than or equal to 400 mg/dl. Animals received, on average, 2000 islet equivalents (150 $\mu$m diameter islet) (this is a minimal dosage) encapsulated in 2 capsules totaling 6 cm in length.

Because of reduced cell necrosis with inner supported capsules, a shorter capsule length can be used to achieve a given level of delivery. With large diameter 700 $\mu$m diameter capsules, use of an inner support enabled a 5-fold reduction in length from 30 cm to 6 cm using at a similar cell density (approximately 7% islet/alginate).

The animals were monitored for weight loss, blood glucose and urinary glucose. Animals showed improvement in blood glucose, decrease in urinary glucose and ketones, and gained weight. Despite the use of the large diameter capsule, none of the animals became hypoglycemic during the course of the experiment, whereas in the absence of an inner support, hypoglycemia was often seen in mice with capsules larger than approximately 1.5 mm inside diameter.

Example 7

Perfusion Test

Rat islet cell aggregates were prepared as in example 6 (approximately 7% density $Ca^{++}$ crosslinked alginate) and were loaded in one of three configurations: (1) 3 mm inside diameter fiber without an inner support; (2) 3 mm inside diameter fiber with a silicone finned inner support (prepared as described in example 2); and (3) 3 mm inside diameter fiber with a silicone finned inner support, with the PAN/PVC membrane then being removed, leaving a crosslinked alginate/ICA mixture surrounding the inner support. The three capsule configurations were then placed in separate chambers in a perfusion system wherein they were perfused with media (MEM) initially containing 100 mg/dl glucose at a flow rate of 0.5 ml/min. Media was collected in a fraction collector for later insulin and glucose assay by RIA and glucose oxidase respectively.

After an initial period of basal perfusion, the media was changed to one containing 300 mg/dl glucose for 40 minutes at which time media was switched back to 100 mg/dl. Insulin release from the configurations was measured as a function of time and is shown in FIGS. 8A, 8B, 8C and 8D.

Configuration (1), without the inner support (FIG. 8A), displayed a very slow insulin response to the change in perfusate glucose concentration— presumably due to the large diffusion distances with their resulting gradients, and to the large internal sink for insulin build-up. Both configurations (2) (FIGS. 8B, 8C) and (3) (FIG. 8D) showed much more rapid response to both upward and downward changes in perfusate glucose concentration, with little differences seen between the two.

Example 8

Stress-Deflection Test

Figure 9:
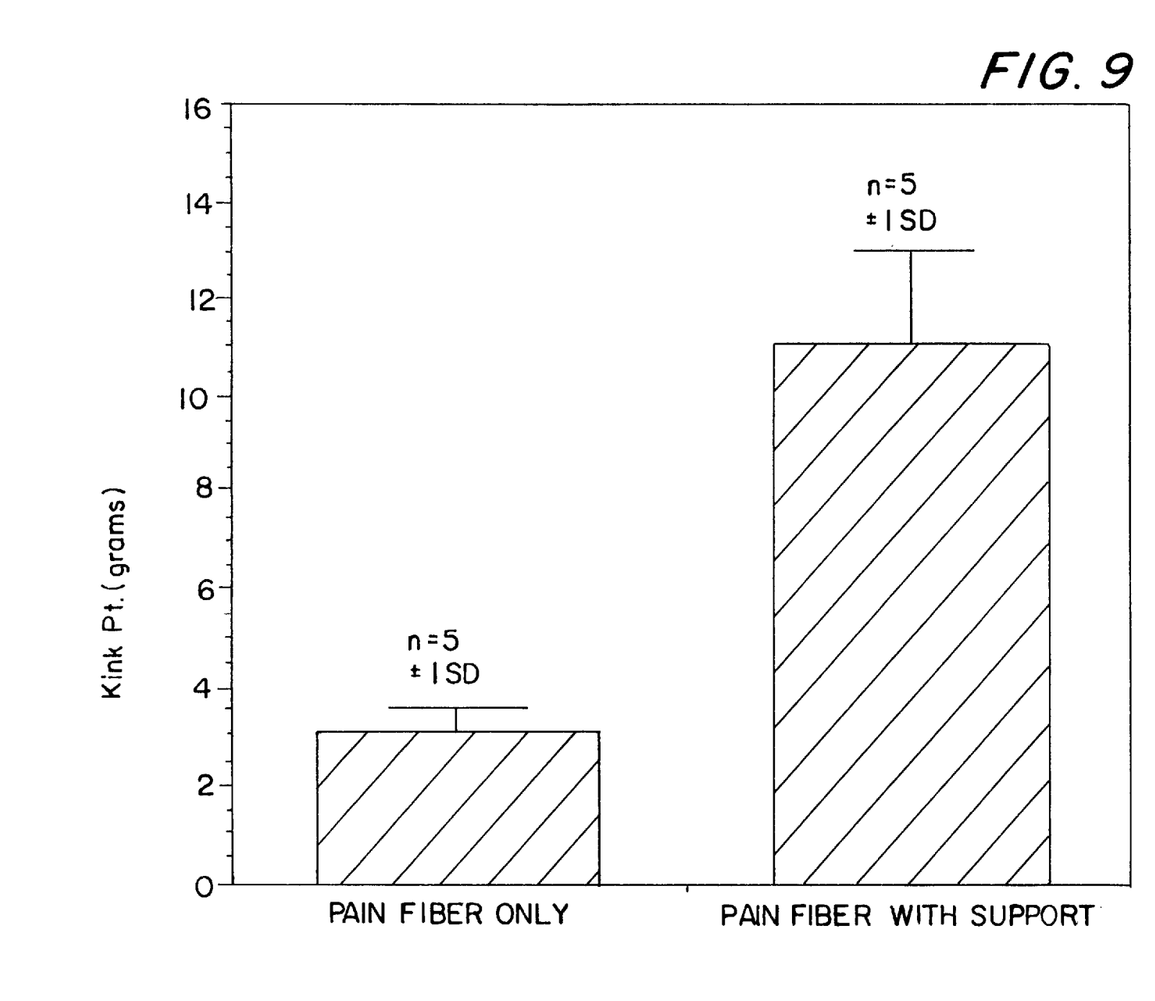
FIG. 9 is a graph comparing the weight required to kink (kink point) an inner supported capsule and a non-inner supported capsule.

A three point tester was used to measure stress-deflection strength of inner supported capsules compared to non-inner supported capsules. As shown in FIG. 9, a greater weight was required to kink inner supported capsules than otherwise identical non-inner supported capsules.

What is claimed is:

1. A biocompatible cell capsule for implantation, comprising:

(a) a capsule jacket connected to a chamber top at one end and chamber bottom at the other end enclosing a cell chamber, (b) the capsule jacket comprising at least one semipermeable surface across which biologically active molecules can be delivered, and (c) an inner support having two ends and extending through the cell chamber such that one end is connected to the chamber top and other end is connected to the chamber bottom, said inner support providing tensile strength to the capsule, and said inner support comprising a filling means for introducing cells or cell-sustaining substances into said chamber and a vent means for escape of air from said chamber as the cells or cell-sustaining substances are introduced.

2. The capsule of claim 1 wherein the cell chamber top comprises a top sealing fitting and the cell chamber bottom comprises a bottom sealing fitting.

3. The capsule of claim 2 wherein the capsule is tubular, the chamber has a longitudinal axis running between the top sealing fitting and the bottom sealing fitting and wherein the inner support is cylindrical and arranged concentrically with the longitudinal axis.

4. The capsule of claim 1 wherein the inner support is coated with a cell-adhesive substance or a cell-viability-enhancing substance.

5. The capsule of claim 1 wherein the inner support is a tube and wherein the filling means comprises at least one filling port and at least one channel through the tube, the channel having an opening which communicates with the cell chamber, and the channel being aligned concentrically with the at least one filling port.

6. The capsule of claim 1 further comprising a tether for retrieval.

7. The capsule of claim 6 wherein said tether is integrally formed with the inner support.

8. The capsule of claim 1 wherein the capsule is immunoisolatory.

9. The capsule of claim 5 wherein the vent means comprises at least one vent port and at least one channel through the tube, the channel having an opening which communicates with the cell chamber, and the channel being aligned concentrically with the at least one vent port.

10. The capsule of either claim 5 or 9 wherein the inner support is a tube and the filling means and the vent means comprise a first channel and a second channel, respectively, wherein the first channel is aligned concentrically with the filling port, and the second channel is aligned concentrically with the vent port.

* * * * *